United States Patent

Habermeier et al.

[11] 3,975,397
[45] Aug. 17, 1976

[54] HETEROCYCLIC TRIGLYCIDYL COMPOUNDS AND PROCESS

[75] Inventors: Juergen Habermeier, Pfeffingen; Daniel Porret, Binningen, both of Switzerland

[73] Assignee: Ciba-Geigy Corporation, Ardsley, N.Y.

[22] Filed: Mar. 14, 1974

[21] Appl. No.: 540,291

Related U.S. Application Data

[62] Division of Ser. No. 238,982, March 28, 1972, Pat. No. 3,821,243.

[30] Foreign Application Priority Data

Apr. 14, 1971 Switzerland............ 5398/71

[52] U.S. Cl............ 260/309.5; 260/2 EP
[51] Int. Cl.² ............ C07D 49/32
[58] Field of Search .............. 260/309.5

[56] References Cited
UNITED STATES PATENTS 3,542,803  11/1970  Porret ............ 260/309.5
3,925,407  12/1975  Stockinger et al. ............ 260/309.5

*Primary Examiner*—Ethel G. Love
*Attorney, Agent, or Firm*—Vincent J. Cavalieri

[57] ABSTRACT

The invention relates to new triglycidyl compounds of the formula:

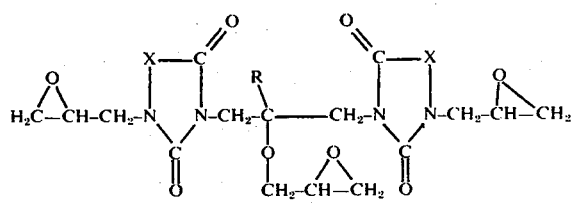

wherein X represents a bivalent alkylene group required for the formation of a 5- or 6-membered heterocycle, and R represents hydrogen or an alkyl group having 1 to 4 carbon atoms.

The new triglycidyl compounds are stable in storage and from them are obtained, after curing, synthetic materials having good mechanical strength and high dimensional stability under heat.

2 Claims, No Drawings

HETEROCYCLIC TRIGLYCIDYL COMPOUNDS AND PROCESS

This is a divisional of application Ser. No. 238,982, filed on Mar. 28, 1972 now U.S. Pat. No. 3,821,243.

The invention relates to new heterocyclic triglycidyl compounds, to a process for their production, as well as to the use thereof.

Heterocyclic compounds containing glycidyl groups are known, e.g. from the German Offenlegungsschriften 1,932,305 and 1,932,306, as well as from the French Pat. No. 1,394,438 and from the Swiss Pat. No. 345,347. The processes for the production of such compounds are not satisfactory in all cases as they are mostly expensive processes. The products produced by the prior known processes frequently present problems with regard to storage, and are not always easy to process. Furthermore, the cured products often do not satisfy the mechanical requirements. It has now been found that good storage-stable heterocyclic triglycidyl compounds possessing after curing high mechanical strength with high dimensional stability under heat and corresponding to formula I:

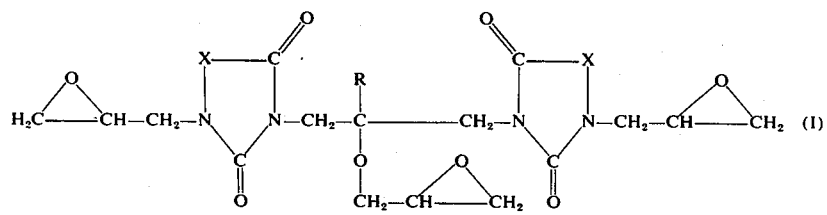

wherein X represents a bivalent alkylene group required for the formation of a 5- or 6-membered heterocycle, and R represents hydrogen or an alkyl group having 1 to 4 carbon atoms, are surprisingly easily obtained by the reaction of compounds of formula II:

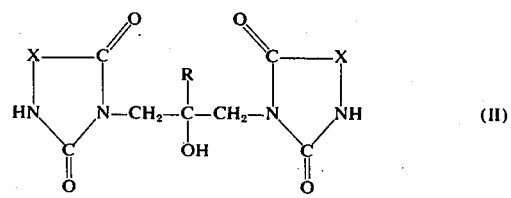

with epihalogenhydrin with elimination of hydrogen halide.

The symbol X in formulae I and II preferably represents one of the following groups:

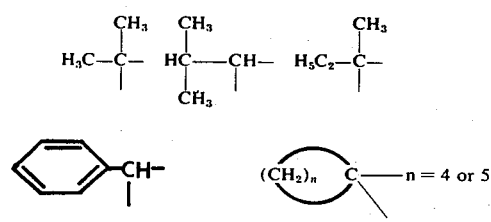

The symbol R preferably represents hydrogen or the methyl group. Particularly advantageous is the compound wherein X stands for the group:

and R stands for hydrogen.

The new triglycidyl compounds are as a rule clear colourless to brown-coloured liquids which are highly viscous at room temperature and do not crystallise out.

They can be easily processed at temperatures of 60° – 120°C together with curing agents such as dicarboxylic acid anhydrides, e.g., phthalic acid anhydride or hexahydrophthalic acid anhydride, to obtain curable mixtures from which are produced, after curing, mechanically and electrically high-grade shaped materials. They are applicable, in particular, for the production of laminating resins, moulding materials, casting resins, and lacquer resins.

The starting materials of formula II for the production process according to the invention are likewise new, and can be obtained by the following procedures:

A. 2 Moles of a cycloureid of formula III:

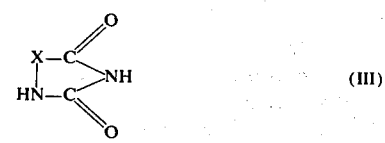

are condensed with 1 mole of 1,3-dichloropropan-2-ol containing in 2-position the radical R.

B. 1 Mole of a cycloureid of formula III is reacted with 1 mole of an epihalogenhydrin in the presence of alkali to give the corresponding monoglycidyl compound. To this is then added 1 further mole of the compound of formula III.

C. 1 Mole of a cycloureid of formula III is converted with 1 mole of an epihalogenhydrin into the corresponding monohalogenhydrin compound, and this compound converted with a further mole of the compound of formula III into a compound of formula II.

D. 2 Moles of a cycloureid of formula III are condensed with 1 mole of epihalogenhydrin with elimination of hydrogen halide.

The process according to the invention for the production of the compounds of formula I is advantageously carried out with azeotropic removal of water in the presence of a hydrogen halide acceptor. Suitable as such is, for example, alkali hydroxide, most simply sodium hydroxide in an equivalent amount or with a slight excess (5 – 30%). The epihalogenhydrin used is preferably epichlorhydrin. A further addition is made, optionally, of a catalyst, e.g., a quaternary ammonium halide such as tetramethylammonium hydroxide, tetraethylammonium bromide, or benzyltrimethylammonium chloride.

If the starting products of formula II are produced by the method D, then it is possible with the addition of the appropriate amount of epihalogenhydrin to obtain the final products of formula I with a single-stage process.

The production of certain starting materials of formula II is described in the following examples:

A. Production of 1,3-bis-(5',5'-dimethylhydantoinyl-3')propan-2-ol

Into a 4-liter glass apparatus fitted with stirrer, thermometer and intensive-cooler is placed, at room temperature, a mixture of 520 g of glycerin dichlorohydrin (1,3-dichloropropan-2-ol) 95% according to gas chromatogram [3.83 moles], 981 g of 5,5-dimethyl-hydantoin, 99.5% [7.66 moles], 582 g of finely ground anhydrous potassium carbonate [4.21 moles] and 960 ml of commercial dimethylformamide. The paste-like mixture is heated to 120°C with slow stirring; as heating proceeds, the mixture becomes thinly liquid. There then occurs immediately an exothermic reaction with an intense evolution of $CO_2$. The heating-bath is removed and the pasty mass, which is tending to thicken, vigorously stirred. After removal of the heating-bath, the temperature rises to 124° – 126°C. The exothermic reaction subsides after about 25 – 30 minutes, and the temperature of the reaction mixture decreases to 116°C. Stirring is carried out for a further 5 hours at 126°C to complete the reaction; and the hot reaction mixture is then filtered, to separate potassium chloride, through a porcelain suction filter.

The mixture is concentrated to dryness in a rotary evaporator at 70° – 80°C under a water-jet vacuum; the product is thus obtained as a clear, slightly yellow-colored melt, which spontaneously crystallizes out in the heat. To effect the removal of volatile constituents, drying is performed at 90°C and 0.2 Torr until constant weight is obtained.

An amount of 1212.6 g of a colorless to pale yellow crude crystallizate (theory: 1196.5 g) is obtained, which melts at 142°C ("Mettler FP 51"). This crude product still contains some potassium chloride and unreacted starting products.

The elementary analysis shows: 46.8% C; 6.5% H; 16.1% N and 5.8% ash (calculated: 50.0% C; 6.4% H; 17.9% N).

The content of the desired bishydantoin in the crude product is accordingly about 86%.

For purification, the crude product can be recrystallized from 550 g of water. Thus obtained are 716.5 g (corresponding to 60.6% of the theoretical amount, relative to the applied dimethylhydantoin) of purified product.

The thus purified 1,2-bis-(5',5'-dimethyl-hydantoinyl-3')-propan-2-ol (= 3,3'-(β-hydroxypropylene)-5,5-dimethylhydantoin) of formula IV:

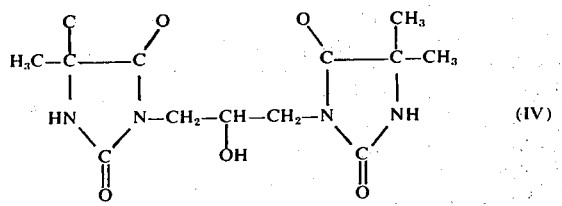

melts at 178° – 181°C.

The elementary analysis shows: Found: 49.5% C 6.4% H 17.6% N 1.1% ash. Calculated: 50.0% C 6.4% H 17.9% N 0% ash.

B. Production of 1,3-bis-(5',5'-dimethyl-hydantoinyl-3')-propan-2-ol

A solution of 1 mole (185 g) of 3-glycidyl-5,5-dimethylhydantoin (epoxide content: 5.4 epoxide equivalents/kg) in 128 ml of dimethylformamide is stirred at 100°C. In the course of 30 minutes, 128 g of dimethylhydantoin are added in small portions. The reaction is exothermic and the heating bath can therefore be removed; the temperature then rises to 130°C. After the exothermic reaction has subsided, stirring is continued for 5 hours at 130°C; the clear pale yellow reaction mixture is afterwards concentrated at 70°C under a water-jet vacuum to dryness, and recrystallized from 150 ml of water. In this manner are obtained, after drying at 100°C in vacuo, 152.8 g of a fine colorless crystallizate (49% of the theoretical amount), which melts at 185.6°C ("Mettler FP 51").

The elementary analysis shows that the obtained product is 1,3-bis-(5',5'-dimethyl-hydantoinyl-3')-propan-2-ol:

Found: 49.9% C 6.6% H 17.8% N. Calculated: 50.0% C 6.5% H 17.9% N.

C 1. Production of 1,3-bis-(5',5'-dimethyl-hydantoinyl-3')propan-2-ol

A solution of 640.5 g of 5,5-dimethyl-hydantoin (5.0 moles) and 3.0 g of potassium chloride in 600 ml of water is stirred at 95°C. To this clear colorless solution are then added dropwise, within 30 minutes, 647.5 g of epichlorhydrin (7.0 moles). Stirring is subsequently carried out for a further 240 minutes at 97°C. The hot reaction mixture is then filtered off, and the clear pale yellow solution completely concentrated at 70°C to dryness under a water-jet vacuum in a rotary evaporator. The mass is afterwards dried at 65°C under 0.15 Torr until constant weight obtains. In this way are obtained 1103 g of a clear, slightly yellow, highly viscous liquid (100% of the theoretical amount), which gradually fully crystallizes to form a white crystal mass. On the basis of the chlorine analysis, the purity of the product is 90.2% (found: 14.5% chlorine, calculated: 16.07%). The remainder consists of the starting substances; there is moreover present a small proportion of 3-glycidyl-5,5-dimethyl-hydantoin, which was determined by epoxide titration (found: 0.2 epoxide equivalents/kg). The proton-magnetic resonance spectrum [60 Mc H-NMR, taken in deuterochloroform ($CDCl_3$) at 35°C with tetramethylsilane as the standard (TMS)] indicates, by the presence of the following signals, that the structure of formula V is in agreement:

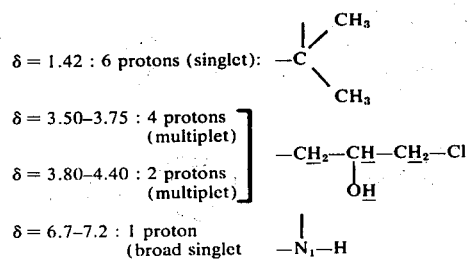

Furthermore, the mass spectrum verifies the presence of the structure according to formula V by the existance of the molecule ion at 221 (= M + H) ME (units of mass) (theoretical molecular weight = 220.7) and of fragment ions at 205 ME (= M — CH₃), 184 ME (= M — HCl), 177 (= M — NHCO), etc.

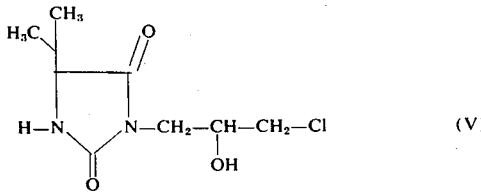

A mixture of 489.5 g of the stated 90.2% 3-(2'-hydroxy-3'-chloro-n-propyl)-5,5-dimethyl-hydantoin (2.0 moles), 207.5 g of 5,5-dimethyl-hydantoin, 152 g of anhydrous finely ground potassium carbonate and 300 ml of dimethylformamide is heated, with stirring, to 120°C. There occurs an intense evolution of $CO_2$, and the reaction mixture is stirred for a total period of 5 hours at 121° – 128°C. Processing is carried out as described in detail under A. As crude product are obtained 623.5 g of a colorless crystal mass (99.8% of the theoretical amount), which contains the desired product with a degree of purity of about 92% (calculated from the elementary analysis). To effect the purification of the product, it is recrystallized from 310 ml of water. An amount of 465.0 g (corresponding to 73% of the theoretical amount) of a fine colourless crystallizate is obtained, which melts at 186° – 187°C. The elementary analysis shows:

Found: 49.6% C 6.4% H 17.6% N. Calculated: 49.9% C 6.4% H 17.9% N.

The product is accordingly identical to the 1,3-bis-(5',5'-dimethyl-hydantoinyl-3')-propan-2-ol produced according to A. and B. The proton-magnetic resonance spectrum (60 Mc-HNMR, taken in $DMSO_{d-6}$ against TMS) confirms moreover, by the presence of the following signals, the structure of formula IV:

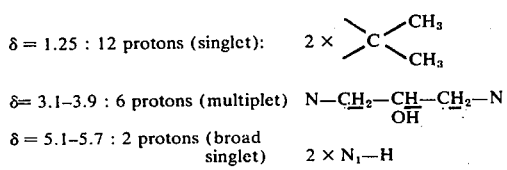

C 2. Production of 1,3-bis-(5',5'-dimethyl-hydantoinyl-3')-2-methylpropan-2-ol.

As described under C 1., 106.6 g of β-methylepichlorhydrin (1.0 mole) are reacted with 128.1 g of 5,5-dimethyl-hydantoin in 140 ml of dimethylformamide, with employment of 1 g of lithium chloride as catalyst. After the dropwise addition of the epoxide, stirring is performed for a further 5 hours at 128°–130°C. Processing is carried out as described under A., and 206 g (88% of the theoretical amount) of a yellow, clear, highly viscous melt are obtained as the crude product, the purity of which, on the basis of the nuclear-resonance spectrum and electroanalysis, is 72%.

A mixture of 193.5 g of this crude 3-(2'-hydroxy-2'-methyl-3'-chloro-n-propyl)-5,5-dimethylhydantoin (corresponding to 0.592 moles), 62.8 g of finely powdered anhydrous potassium carbonate, 125 ml of dimethylformamide and 75.8 g of 5,5-dimethyl-hydantoin (0.592 moles) is stirred for 10 hours at 125°C. An intense evolution of $CO_2$ is, as usual, initially observed, which gradually decreases. The mixture is afterwards cooled to 80°C, and 330 ml of water are added, the whole being then cooled, with stirring, to 0°–5°C. In the course of a few hours, the desired product crystallizes out in the form of a colorless precipitate. This is filtered off, and dried at 70°C under 20 Torr until constant weight is obtained. An amount of 118 g (corresponding to 61% of the theoretical amount) of a colorless powder is obtained which melts at 162°–164°C. The mass spectrum shows the molecular ion (M) enlarged by one proton at 327 units of mass (ME = Masseneinheiten = units of mass), which is in agreement with the molecular weight of 326.4. Furthermore, the following fragmentations, amongst others, can be recognised: 311 (= M—CH₃), 309 (327—H₂O), 308 (M-H₂O), 293 (311-H₂O); 185 (fragmentation between C₁ and C₂ of the bridge); etc. Likewise, the proton magnetic resonance spectrum (60 Mc HNMR, in $CDCl_3$ against TMS), shows that the new bishydantoin has the structure according to the formula VI.

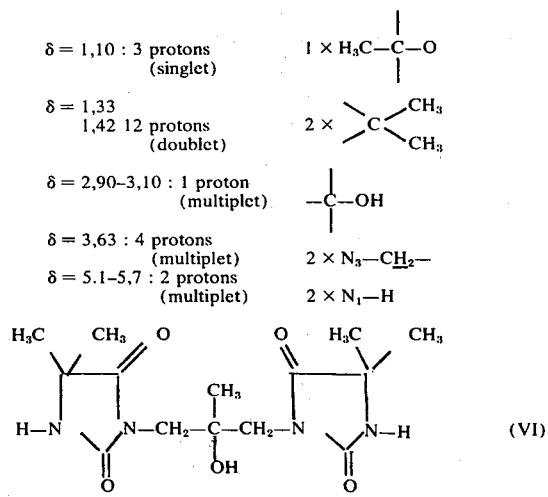

D 1. 1,3-bis-(5',5'-dimethyl-hydantoinyl-3')-propan-2-ol

In a 6-liter four-necked flask fitted with stirrer, thermometer, reflux condenser and dropping-funnel, 1793 g of 5,5-dimethyl-hydantoin (14.0 moles), 1015 g of finely powdered anhydrous potassium carbonate (7.35 moles), 10 g of potassium chloride and 1750 ml of dimethylformamide are stirred at 110°C. An addition is made dropwise to this mixture, within 90 minutes and with vigorous stirring, of 712 g of epichlorhydrin (7.7 moles). The reaction becomes exothermic, and an intense evolution of $CO_2$ commences. The heating bath is removed and the temperature rises to 135°C. The exothermic reaction quickly subsides after completion of the dropwise addition. In order to complete the reaction, stirring is continued for 5 hours at 125°C. The reaction mixture is diluted with 300 ml of dimethylformamide; whilst it is still hot, it is filtered off from the potassium chloride, and subsequently concentrated to dryness at 120°C in the rotary evaporator under a water-jet vacuum. It is afterwards dried at 120°C under 0.2 Torr to constant weight. In this manner are obtained 2307 g of a crude product, which is recrystallized from 1200 ml of water. An amount of 1351 g (62% of the theoretical amount) of a colorless fine crystallizate (without processing of the mother liquor) is obtained. The purified product melts at 190°–191°C. The elementary analysis too shows that the product is pure and corresponds to formula IV. This is also proved by identical proton magnetic resonance spectra.

Elementary analysis: Found: 49.7% C 6.5% H 17.7% N. Calculated: 49.9% C 6.5% H 17.9% N.

D 2.
1,3-bis-5′,5′-dimethyl-hydantoinyl-3′)-propan-2-ol

The procedure according to D 1. is repeated and the brown-yellow crude product characterized, of which 2307 g are isolated. The product melts at 149°–152°C and the elementary analysis shows that 5.3% or inorganic material is still present. The yield of organic substance is therefore 2185 g (100% of the theoretical amount) which, according to the elementary analysis, consists to the extent of about 95% of the desired product. In order to remove the inorganic materials and the colored by-products, the crude product is finely ground in a cross beater mill, and then stirred together with 1725 ml of deionized water at room temperature to obtain a homogeneous mass. After 1 hour's stirring the mass is filtered through a suction filter, and intensely dried by suction. A colorless filter cake is obtained, which is crushed, and dried in 24 hours at 100°C under 30 Torr. The purified product is obtained in 71% yield (1520 g). The product melts at 181°–183°C, and the content of inorganic material is only 0.9%. For glycidylation reactions, the thus purified materials can be used exactly as the material produced according to D 1.

D 3.
1,3-bis-(5′-methyl-5′-ethyl-hydantoinyl-3′-propan-2-ol

Analogously to D 1., 148.3 g of 5-methyl-5-ethyl-hydantoin (98.5%) (1.80 moles) containing 4% of sodium chloride are reacted with 46.25 g of epichlorhydrin (0.5 moles) in 500 ml of dimethylformamide under the action of 71.2 g of potassium carbonate (0.515 moles).

The reaction is performed and the reaction mixture processed according to D 1. An amount of 172.9 g of a brittle, clear, light-brown glass is thus obtained (theory: 170.2 g), which still contains as an impurity about 1.6% of dimethylformamide. This crude product is further processed in its present form. The proton-magnetic resonance spectrum (60 Mo—HNMR) shows, besides a trace of dimethylformamide (δ = 2.9 and 3.0), the presence of the desired molecule (formula VII) by the signals at δ = 0.8 – 1.05 (multiplet), δ =1.45 (singlet), δ =1.55 – 2.0 (multiplet), δ = 3.5 – 3.7 (multiplet), δ = 4.0 – 4.2 (multiplet) and δ = 5.5 – 6.2 (multiplet):

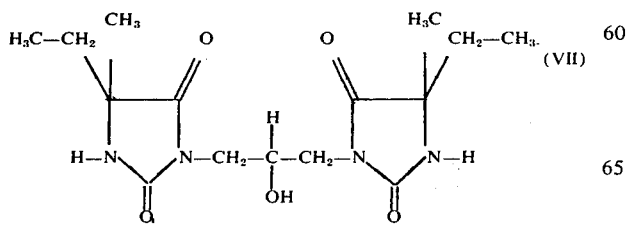

D 4. 1,3-bis-(5′-isopropyl-hydantoinyl-3′)-propan-2-ol

As described under D 1., a mixture of 142.2 g of 5-isopropylhydantoin (1 mole), 46.25 g of epichlorhydrin (0.5 moles), 71.2 g of potassium carbonate (0.515 moles) and 0.4 g of potassium chloride in 500 ml of dimethylformamide is caused to react. The processing to obtain the crude product, which requires no further purification, is carried out likewise as described under D 1. Thus obtained are 171.8 g of a clear, gold-yellow, glass-like product (theory: 170.2 g), which still contains about 1% of dimethylformamide as impurity. The proton-magnetic resonance spectrum shows, in agreement with the following structure (formula VIII), the following signals: δ = 0.8 – 1.2 (triplet), δ = 2.0 – 2.3 (multiplet), δ = 6.0 – 6.3 (multiplet).

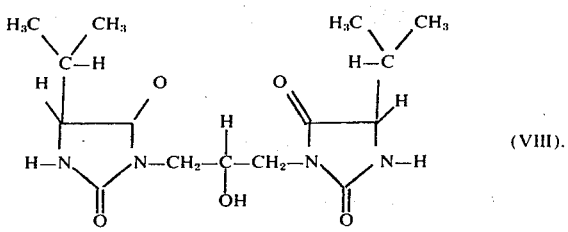

D 5.
1,3-(5,5′-pentamethylene-hydantoinyl-3′)-propan-2-ol

By the procedure according to D 1., the addition and condensation are effected of 92.5 g of epichlorhydrin (1 mole) with 336.4 g of 5,5-pentamethylenehydantoin (2 moles) in 900 ml of dimethylformamide, with the addition of 142.3 g of potassium carbonate and 0.8 g of potassium chloride. Processing is carried out as described under D 1. Thus obtained are 409.9 g of the desired bishydantoin (theory: 392.4 g), which still contains about 5% of dimethylformamide, as a clear-yellow crystal powder. For purification, recrystallization is performed from dioxane/water: 2/1 in the ratio of 1 : 3.5. An amount of 314.5 g (80.2% of theory) of a colorless, dust-fine crystallizate is thus obtained, which melts at 247.1°C (Mettler FP51, 1°/min.).

The elementary analysis shows the following values:

| Found | Calculated |
| --- | --- |
| 57.9% C | 58.1% C |
| 7.3% H | 7.2% H |

The mass spectrum is in agreement with the expected structure; the molecule ion is found at 392 units of mass (M-theory: 392.4%); the fragmentations also agree. The proton-magnetic resonance spectrum (60 Mc-HNMR) shows likewise that the below formula IX is in agreement:

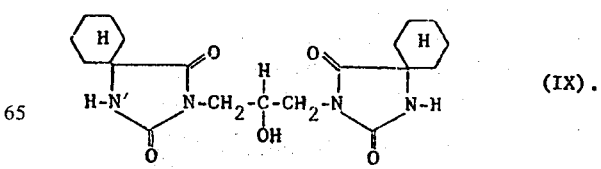

D 6.
1,3-bis-(5,5'-tetramethylene-hydantoinyl-3')-propan-2-ol

In the manner described under D 1., the following mixture is caused to react:
154.2 g of 5,5-tetramethylenehydantoin (1 mole)
46.25 g of epichlorhydrin (0.5 moles),
71.20 g of potassium carbonate (0.515 moles),
0.4 g of potassium chloride,
500 ml of dimethylformamide.

Processing and isolation of the desired bishydantoin are performed likewise as described under D 1. Without further characterization, the crude product is recrystallized direct from 360 ml of dioxane/water: 2:1. An amount of 98 g (54% of theory; without processing of the mother liquor) is obtained of a colorless, fine crystallizate which melts at 185.2°C (Mettler FP 51, 2°/min.). The proton-magnetic resonance spectrum is in agreement with formula X:

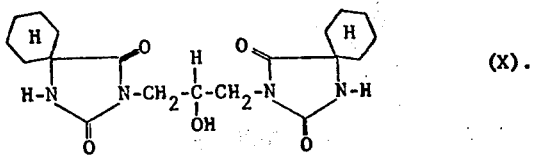

(X).

PRODUCTION EXAMPLES

EXAMPLE 1

In a 6-liter glass apparatus fitted with stirrer, thermometer, dropping funnel, and water separator for circulation-distillation of specifically heavier solvents, and with reflux condenser and vacuum connection, a mixture of 500 g of 1,3-bis-(5',5'-dimethylhydantoinyl-3')-propan-2-ol (1.6 moles) produced by application of one of the previously described procedures, 17 g of 50% aqueous tetramethylammonium chloride and 5328 g of epichlorhydrin (57.6 moles) is stirred for 30 minutes at 90°C. A vigorous circulation distillation at 150°–160°C bath temperature under 50–70 Torr vacuum is then so arranged that there is a temperature of 60°C in the reaction mixture. An addition is then made dropwise in the course of 150 minutes, with vigorous stirring, of 480 g of 50% aqueous sodium hydroxide solution (6.0 moles); in the process of this the water present in the reaction mixture is continuously azeotropically distilled off from the charge, separated from the returning epichlorhydrin, and removed. After completion of the addition of sodium hydroxide solution, distillation is continued for a further 60 minutes with circulation of the epichlorhydrin under the described conditions, until no further traces of water are being separated. The reaction mixture is afterwards cooled to about 40°C. The formed sodium chloride is removed by suction filtration. The epichlorhydrin solution is washed with 500 ml of water. The organic phase is concentrated in the rotary evaporator at 60°–70°C bath temperature under a water-jet vacuum. In order to remove fractions volatile in water vapour, 200 ml of water are added to the mixture, and complete distillation is carried out under the stated conditions. The mixture is subsequently mixed with 100 ml of toluene and fully concentrated by evaporation to remove traces of water. Drying to constant weight is then performed at 65°–70°C in a rotary evaporator under 0.2 Torr. An amount of 770 g of a clear, slightly yellow triglycidyl compound (100% of the theoretical amount), highly viscous at room temperature, is obtained, the epoxide content of the said triglycidyl compound being 6.20 equivalents/kg (99.2% of the theoretical amount).

The new triepoxide does not crystallise out even when standing for 4 months at 5°C and at room temperature. After the addition of acetone and chloroform at the stated temperatures there is after 4 months likewise no detectable tendency for crystallization to occur. The elementary analysis shows a total chlorine content of 1%; further analysis results are: 54.6% C; 6.8% H and 11.0% N (calculated: 54.9% C; 6.7% H and 11.6% N). The proton magnetic resonance spectrum (60 McHNMR, in CDCl$_3$ against TMS) shows by the presence of the following signals, amongst others, that the below given structure is in agreement:

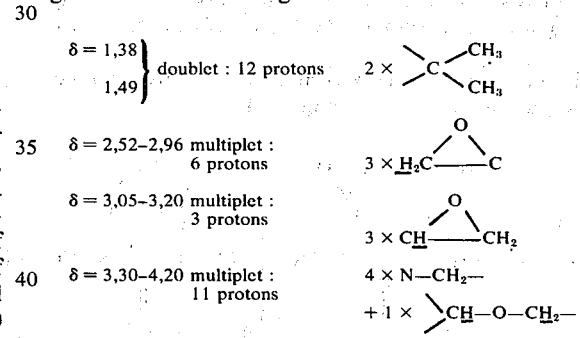

The infra-red spectrum (capillary absorption) too shows by the presence both of the hydantoincarbonyl absorption and of epoxide oscillations and C—O—C— absorptions that the desired substance has been obtained.

The determination of the mean molecular weight by vapor pressure osmometry ("Mechrolab 302 B"; measured in dioxane at 50°C) gives M$_n$ = 470 (theory = 480). Furthermore, a gel permeation chromatogram in tetrahydrofuran shows that the substance is molecularly homogeneous to the extent of 85%.

The new triglycidyl compound accordingly corresponds to formula XI:

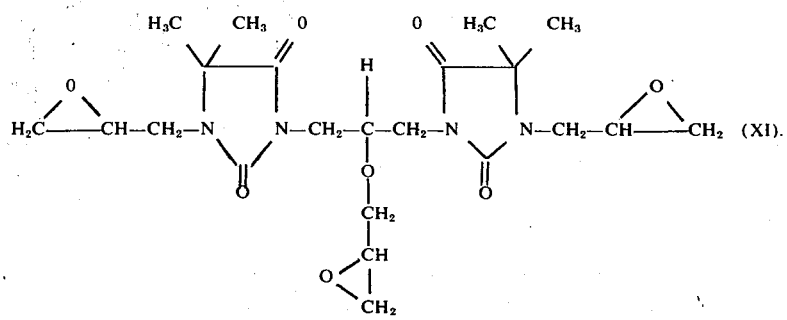

EXAMPLE 2

As in Example 1, 112.5 g of the 1,3-bis-(5',5'-dimethyl-hydantoinyl-3')-2-methyl-propan-2-ol (0.3445 moles) produced as described under C 2. are caused to react with 1435 g of epichlorhydrin (15.5 moles) with the action of 3.8 g of 50% aqueous tetramethylammonium chloride solution. Dehydrohalogenation is performed, according to Example 1, with 103.4 g of 50% aqueous sodium hydroxide solution (1.294 moles). Processing and purification of the new triglycidyl compound are carried out likewise according to Example 1.

An amount of 171 g of a viscous light-brown resin (100% of the theoretical amount) is obtained of which the epoxide content is 5.67 equivalents/kg (93.5% of the theoretical amount). The total chlorine content is 1.5%.

The new epoxide resin consists essentially of molecules corresponding to formula XII:

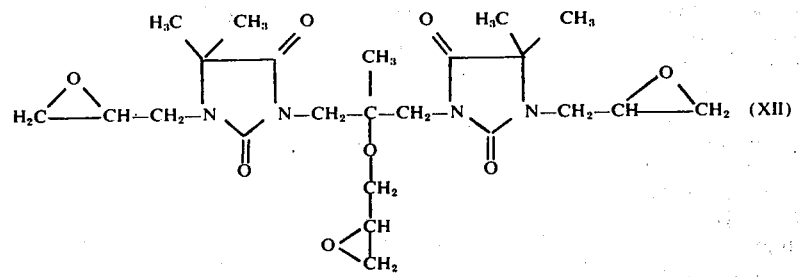

EXAMPLE 3

As described in Example 1, 165.3 g of the bishydantoin (0.485 moles) produced according to D 3 are reacted with 1615 g of epichlorhydrin (17.45 moles) under the catalytic action of 5.2 g of 50% aqueous tetramethylammonium chloride solution. Dehydrochlorination is performed, likewise according to Example 1, with 145.1 g of 50% aqueous sodium hydroxide solution (1.815 moles).

After processing and purification of the product according to Example 1, an amount of 226 g of a clear, viscous, light-brown resin (91.4% of theory) is obtained, of which the epoxide content is 5.84 equiv./kg (99% of theory). The content of total chlorine is 0.9%. The product consists essentially of the triglycidyl compound of the following formula VIII:

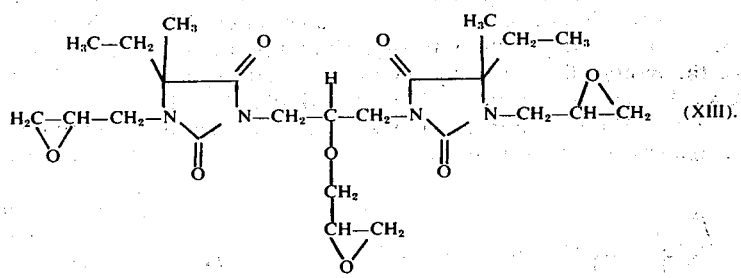

EXAMPLE 4

An amount of 170 g of the bishydantoin (0.495 moles) obtained according to D 4 is reacted according to Example 1 with 1663 g of epichlorhydrin (17.98 moles), 5.3 g of 50% aqueous tetramethylammonium chloride solution and 149.6 g of 50% aqueous sodium hydroxide solution (1.869 moles). Obtained after the usual processing are 225.5 g of a clear light-yellow triglycidyl compound of formula XIV (89.6% of theory) having 5.32 epoxide equivalents/kg (90.2% of theory).

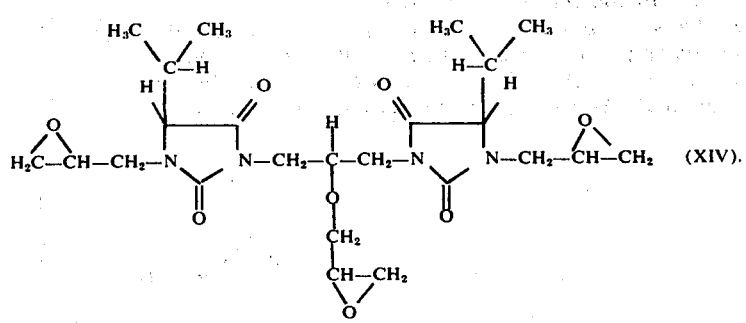

EXAMPLE 5

The following substances are reacted analogously to the procedure described in Example 1:
196.2 g of the bishydantoin (0.5 moles) produced according to Example 5,
1665 g of epichlorhydrin (18 moles),
5.3 g of 50% aqueous tetramethylammonium chloride solution,
149.7 g of 50% aqueous sodium hydroxide solution (1.87 moles).

The reaction procedure and processing according to Example 1 yield the following:
253.5 g of a light-ochre colored resin (90.5% of theory),
5.26 epoxide equivalents/kg (98.4% of theory).

According to the MNR-spectrum, the new triglycidyl derivative corresponds to the following formula XV:

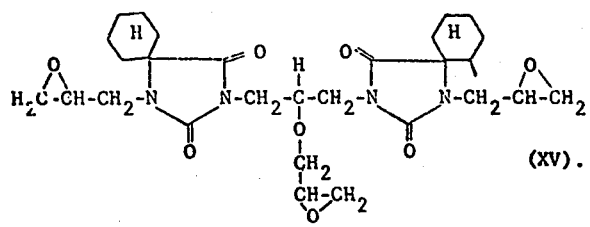

(XV).

EXAMPLE 6

The following are reacted as described in Example 1:
96 g of the bishydantoin (0.263 moles) produced according to D 6.,
877 g of epichlorhydrin (9.48 moles),
2.8 g of 50% aqueous tetramethylammonium chloride solution,
78.8 g of 50% aqueous sodium hydroxide solution (0.985 moles).

After processing as already described, an amount of 139.5 g (99.6% of theory) of a clear, pale yellow resin is obtained containing 5.39 epoxide equivalents/kg, and corresponding essentially to the following formula XVI:

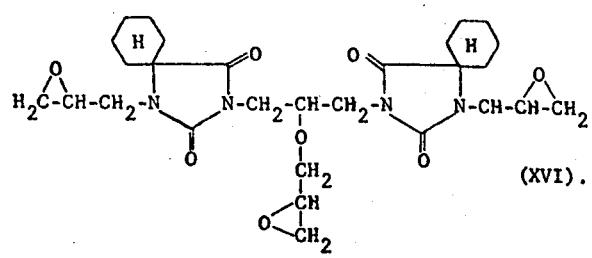

(XVI).

APPLICATION EXAMPLES

EXAMPLE I

A mixture is prepared of 54 parts of the triepoxide produced according to Example 1 with 6.2 epoxide equivalents/kg and 46 parts of phthalic acid anhydride. The mixture is processed at 120°–130°C, with stirring, to obtain a homogeneous, practically colorless melt, which is poured into aluminum moulds preheated to 120°C. The melt is cured in 2 hours at 120°C and in 11 hours at 150°C, and clear transparent moulded articles are obtained having the following mechanical properties:

| | |
|---|---|
| bending strength (VSM 77,103) | 13–16 kp/mm$^2$ |
| deflection (VSM 77,103) | 4.5–5.1 mm |
| water absorption (4 days/20°C) | 0.7% |

EXAMPLE II

A clear, practically colorless melt is produced at 50°C from 167 parts of the triepoxide produced according to Example 1 with 6.2 epoxide equivalents/kg and 146 parts of hexahydrophthalic acid anhydride.

To this mixture are added 2 g of benzyldimethylamine, and the homogeneous mixture is poured into aluminum moulds preheated to 100°C. Curing is performed in 2 hours at 100°C, 2 hours at 120°C, and 11 hours at 150°C. The gelling time of a 100 g specimen of the above mixture at 100°C is 20 minutes ("Tecam Gelation Timer"). The obtained moulded articles possess the following properties:

| | |
|---|---|
| bending strength (VSM 77 103) | 11–15 kp/mm$^2$ |
| deflection (VSM 77 103) | 4–6 mm |
| impact bend strength (VSM 77 105) | 12–14 cm.kp/cm$^2$ |
| mechanical dimensional stability at elevated temperature according to Martens (DIN) | 159°C |
| heat distortion (DIN 53 461) | 168–171°C |
| water absorption (4 days/20°C) | 0.5–0.6 % |
| dielectric constants (50 c.p.s.)$E_r$ | |
| at 23°C | 3,6 |
| at 130°C | 3.6 |
| at 165°C | 3.8 |
| dielectric loss factor (50 c.p.c.) tg | |
| at 23°C | 0.008 |
| at 130°C | 0.008 |
| at 165°C | 0.024 |
| current-flow resistance at 25°C | 3.5·10$^{16}$ cm |
| tracking resistance (VDE 0303) | stage KA 3c |
| arc resistance (VDE 0303) | stage L4 |

EXAMPLE III

100 Parts of the triepoxide produced according to Example 2 are mixed, processed and cured, according to Example II, with 83 parts of hexahydrophthalic acid anhydride and 1.5 parts of benzyldimethylamine. Light-yellow clear moulded articles are thus obtained having the following properties:

| | |
|---|---|
| bending strength (VSM 77 103) | 13–17 kp/mm² |
| deflection (VSM 77 103) | 4–6 mm |
| impact bend strength (VSM 77 105) | 14–18.5 cm.kp/cm² |
| heat distortion (DIN 53 461) | 150 °C |
| water absorption (4 days/20°C) | 0.57 % |

EXAMPLE IV

The mixing, processing and curing are carried out, as described in Example II, of 85.6 g of the triepoxide produced according to Example 3 containing 5.84 epoxide equivalents/kg, and 73.3 g of hexahydrophthalic acid anhydride.

By this procedure are obtained light-brown moulded articles having the transparency of glass and possessing the following properties:

| | |
|---|---|
| bending strength (VSM 77103) | 10.8–12.0 kg/mm², |
| deflection (VSM 77103) | 4 –5 mm |
| impact bend strength (VSM 77105) | 10.5–11.75 cm.kp/cm², |
| mechanical dimensional stability at elevated temperatures according to Martens (DIN) | 158°C, |
| heat distorton (DIN 53461) | 160°C, |
| cold water absorption (4 days 23°C) | 0.56% |
| boiling water absorption (1 h/100°C) | 0.42%. |

EXAMPLE V

The mixing, processing and curing are carried out according to Example II of 188.0 g of the triglycidyl compound produced according to Example 4 containing 5.32 epoxide equivalents/kg with 146.5 g of hexahydrophthalic acid anhydride. The obtained clear light-yellow moulded specimens give the following values:

| | |
|---|---|
| arc resistance (ASTM 495) | stage 3, |
| tracking resistance (DIN 53480) | stage KA 3c, |
| cold water absorption (4 days/23°C) | 0.58%, |
| flexural strength (VSM 77103) | 11.25–12.48 kp/mm², |
| deflecton (VSM 77103) | 5.1 – 5.3 mm, |
| impact bend strength (VSM 77105) | 10.3 –10.5 cm.kp/cm², |
| dimensional stability at elevated temperatures according to Martens (DIN) | 146°C, |
| heat distortion (DIN 53461) | 153°C. |

EXAMPLE VI

The mixing, processing and curing are carried out according to Example II of 190.1 g of the epoxide resin produced according to Example 5 containing 5.26 epoxide equivalents/kg with 146.5 g of hexahydrophthalic acid anhydride. In this manner are obtained light, clear moulded specimens having the following properties:

| | |
|---|---|
| flexural strength (VSM 77103) | 10.32–11.68 kp/mm², |

-continued

| | |
|---|---|
| impact bend strength (VSM 77105) | 12.75 cm.kp/cm², |
| dimensional stability at elevated temperatures according to Martens (DIN) | 147°C, |
| heat distortion (DIN 53461) | 153–155°C, |
| water absorption (4 days 23°C) | 0.38 %, |
| water absorption (1 hour at 100°C) | 0.28 %. |
| break down potential (50 c.p.s.) (according to IEC Pub. 243) 20 seconds value | 205–215 kV/cm, |
| tracking resistance (DIN 53480) | KA 3c, |
| arc resistance (ASTM 495) | stage 3, |
| dielectric loss factor, tan δ | |
| at 50°C | 0.0042, |
| at 150°C | 0.024; |
| relative dielectric constants $E_r$, 50 c.p.s. | |
| at 50°C | 3.3, |
| at 100°C | 3.4, |
| at 130°C | 3.4, |
| at 140°C | 3.5, |
| at 150°C | 3.6; |
| specific current-flow resistance $S_p$ (DIN 53482) (Ω.cm) | |
| at 23°C | $5.10^{16}$ |
| at 80°C | $4.10^{15}$. |

EXAMPLE VII

The mixing, processing and curing are carried out according to Example II of 92.8 g of the triepoxide produced according to Example 6 containing 5.39 epoxide equivalents/kg and 73.2 g of hexahydrophthalic acid anhydride. The obtained moulded articles have the following properties:

| | |
|---|---|
| flexural strength (VSM 77103) | 10.22–13.27 kp/mm², |
| deflection (VSM 77103) | 4.1 –5.9 mm, |
| impact bend strength (VSM 77105) | 11.75–15.75 cm.kp/cm², |
| dimensional stability at elevated temperatures according to Martens (DIN) | 147°C, |
| heat distortion (DIN 53461) | 156–158°C, |
| water absorption (4 days at 23°C) | 0.50%, |
| water absorption (1 hour at 100°C) | 0.37%. |

EXAMPLE VIII

Comparison Example a. A mixture is produced, as described in Example II, of 100 g of commercially produced triglycidylisocyanurate containing 9.3 epoxide equivalents/kg and 135 g of hexahydrophthalic acid anhydride. The processing and curing are performed according to Example II.

b. In accordance with DOS No. 1,932,305, 100 g of 1,3-dipropyl-5,7-diglycidylglycoluryl are mixed, whilst heating is applied, with 41.6 g of hexahydrophthalic acid anhydride, and the mixture is then cured in the above mentioned aluminum moulds in 16 hours at 140°C.

The results of the comparison tests are given in the following table:

| Properties | Example II | Comparison a triglycidyl-isocyanurate (FP 1,394,438 et.al.) | Comparison b 1,3-dipropyl-5,7-diglycidyl-glycol-uril (DOS 1,932,305) |
|---|---|---|---|
| storage stability of the product at 30°C | very good (over 12 months) | poor (2–3 months) | unknown |
| working properties as casting resin | very good viscous, on heating low viscosity | difficult (crystals, insoluble constituents) | (viscous on heating) |
| flexural strength (VSM) Kp/mm² | 11 – 15 | 9 – 10 | 10 – 11 |
| deflection (VSM) | 4–6 | 5 – 6 | — |

-continued

| Properties | Example II | Comparison a triglycidyl-isocyanurate (FP 1,394,438 et.al.) | Comparison b 1,3-dipropyl-5,7-diglycidyl-glycol-uril (DOS 1,932,305) |
|---|---|---|---|
| (mm) impact bend strength $\frac{(cm \cdot kg)/cm^2}{}$ | 12 – 14 | 5 – 7 | — |
| heat distortion (DIN (°C) | 168 – 171 | 175 – 176 | 145 glass-transition temperature |
| diel. constants ER | | | |
| 20°C | 3,6 | — | 3,7 |
| 140°C | 3,6 | 3,6 | 3,7 |
| 165°C | 3,8 | — | — |
| dielectric loss factor tan δ | | | |
| 20°C | 0,008 | — | 0,008 |
| 140°C | 0,008 | 0,01 | 0,022 |
| current-flow resistance(Ω. cm) 25°C | $3,5.10^{16}$ | $7.10^{16}$ | $6.4.10^{15}$ |

It can be seen from the table that a. the working properties as a casting resin are better in the case of the mixture according to Example II;

b. the mechanical strengths of the mixture cured according to Example II are in some cases appreciably higher than in the case of the comparison substances — particularly with regard to Comparison (a);

c. the electric properties, especially at temperatures above 140°C, are better in the case of the specimen cured according to Example II than in the case of the glycoluril derivative.

We claim:

1. A process for the preparation of a binuclear heterocyclic compound of the formula

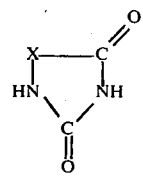

wherein X is

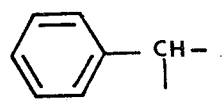

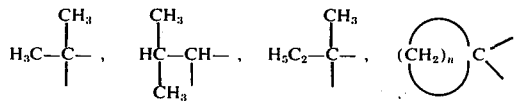

n=4 or 5 comprising reacting a hydantoin compound of the formula wherein X is

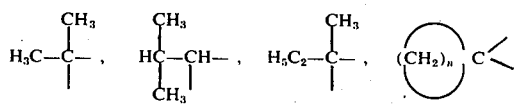

n=4 or 5 with 1 mole of an epihalohydrin having an R radical in the 2 position wherein R is hydrogan or an alkyl of 1 to 4 carbon atoms, to yield the corresponding monohalohydrin compound, said compound being condensed with 1 more mole of said hydantoin compound.

2. The process according to claim 1 wherein R is hydrogen or methyl.

* * * * *